United States Patent [19]

Besecke et al.

[11] Patent Number: 4,463,159
[45] Date of Patent: Jul. 31, 1984

[54] POLYARYLENE ESTERS CONTAINING PHOSPHORUS

[75] Inventors: Siegmund Besecke, Seeheim-Jugenheim; Guenter Schroeder, Ober-Ramstadt; Werner Ude, Darmstadt-Arheilgen; Winfried Wunderlich, Rossdorf, all of Fed. Rep. of Germany

[73] Assignee: Röhm GmbH, Darmstadt, Fed. Rep. of Germany

[21] Appl. No.: 499,526

[22] Filed: May 31, 1983

[30] Foreign Application Priority Data

Jun. 16, 1982 [DE] Fed. Rep. of Germany ....... 3222571

[51] Int. Cl.$^3$ .............................................. C08G 63/68
[52] U.S. Cl. .................... 528/167; 528/169; 528/398
[58] Field of Search ................. 528/167, 169, 398

[56] References Cited

U.S. PATENT DOCUMENTS

| | | | |
|---|---|---|---|
| 3,847,866 | 11/1974 | Bredereck et al. | 528/167 |
| 4,087,408 | 5/1978 | Moedritzer | 528/169 |
| 4,123,420 | 10/1978 | Kyo et al. | 528/167 |
| 4,210,740 | 7/1980 | Couchord | 528/167 |
| 4,255,555 | 3/1981 | Salee et al. | 528/167 |
| 4,278,785 | 7/1981 | Rosenfeld | 528/167 |
| 4,328,174 | 5/1982 | Schmidt et al. | 260/930 |

FOREIGN PATENT DOCUMENTS 2925206 1/1981 Fed. Rep. of Germany .
56-65020 6/1981 Japan .

*Primary Examiner*—Lester L. Lee

[57] ABSTRACT

What are disclosed are phosphorus-containing polyarylene esters,

—O—A—O—CO—B—CO]$_n$, wherein A represents at least in part groups of the structure $$\left[\phantom{X}\!\!-\!\!\bigcirc\!\!-\!\!\underset{\underset{R}{|}}{\overset{\overset{O}{\|}}{P}}\!\!-\!\!\bigcirc\!\!-\!\!\phantom{X}\right]_x,$$

wherein x is 0 or 1 and R is aromatic or aliphatic, and wherein B represents either two different aromatic groups or at least one group with the structure —C$_6$H$_4$—R'—C$_6$H$_4$—, wherein R' is a bridging link of the group —O—, —S—, —SO$_2$—, —CO—, or isopropylidene, and wherein n is greater than 20, which esters have a phosphorus content of over 1 weight percent, are distinguished by improved thermoplastic processability, and are prepared by condensation of HO—A—OH, for example with ClCO—B—COCl in the presence of a base.

8 Claims, No Drawings

POLYARYLENE ESTERS CONTAINING PHOSPHORUS

The present invention relates to polyarylene esters containing phosphorus, which esters are of interest as highly heat-resistant and flame-retardant thermoplastic materials.

From published German patent application DOS 29 25 206, polyester phosphonates are known which, with regard to their properties, belong to the same class of plastics. However, because of their content of phosphonic ester groups, they are dissociated fairly easily by hydrolysis.

Phosphorus-containing polyarylene esters are described in published Japanese patent application 81 65020 and in an article by H. Kondo et al. [European Polymer Journal, 17, 583–588 (1981).] They contain the phosphorus atoms in structures having multiple fused ring which impart pronounced stiffness to the polymer molecule. This results in high softening temperatures which make it necessary to process these materials close to their decomposition temperature.

S. Hashimoto et al. [Kobunshi Kagaku, Eng. Ed., 2, No. 9, 826–834 (1973)] have prepared phosphorus-containing polyarylene esters of the structure

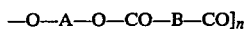

by the Schotten-Baumann condensation of aliphatic or aromatic carboxylic acid chlorides ClCO—B—COCl, wherein B represents an aliphatic or aromatic group, with phosphorus-containing bisphenols HO—A—OH, wherein A represents a group of the structure

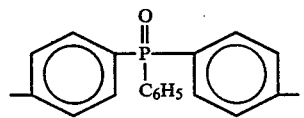

The polyarylene esters obtained tend to crystallize, which raises their melting temperature. The melting temperature of a polyarylene ester with the structure described above, wherein B stands for para-phenylene groups, is about 300° C. On the other hand, the melting temperature of a co-condensate in which about 30 percent of the groups A are replaced by bisphenol A groups is only about 250° C. This reduction of the melting temperature, though desirable from the viewpoint of processability, falls short of being adequate, and it can be had only at the expense of a decrease in the phosphorus content of 28 percent.

The object of the present invention is to lower the melting temperature of phosphorus-containing polyarylene esters further without also reducing their phosphorus content, and to prepare amorphous, thermoplastically processable plastics which have no partially crystalline regions and whose glass transition temperatures are not higher than 200° C. In accordance with the invention, this object is accomplished in that the groups B of the above formula are made up of at least two different aromatic groups or of bridged aromatic groups. The invention thus has as its object phosphorus-containing polyarylene esters of the structure

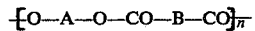

wherein A represents at least in part groups of the structure

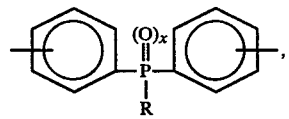

I wherein R represents a lower alkyl group, an aryl group, or an aralkyl group, x is 0 or 1, and the aryl groups optionally carry further substituents, the rest, if any, of A being made up of groups of the structure given for B and wherein B represents at least two different moieties from the group

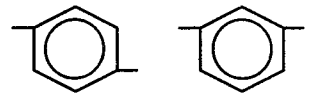

or at least one moiety with the structure

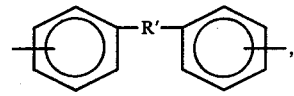

wherein R' is an oxygen atom, a sulfur atom, or a sulfonyl, carbonyl, or isopropylidene bridging group, n has a mean value of over 20, and the phosphorus content is over 1 weight percent. Compounds wherein R' is oxygen, sulfonyl, carbonyl, or isopropylidene are preferred.

One of the polyarylene esters in accordance with the invention, for example,

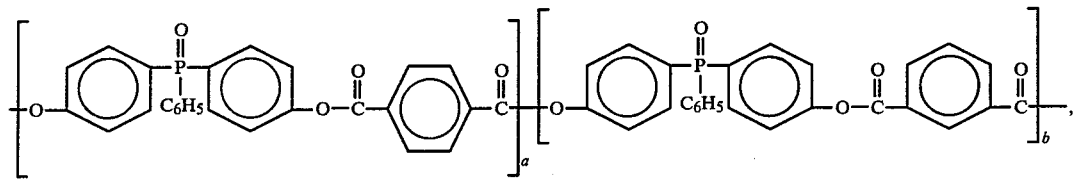

with a ratio of a to b of 1:1, has a phosphorus content of 7.2 weight percent and a glass transition temperature of 175° C., whereas the prior-art polyarylene ester

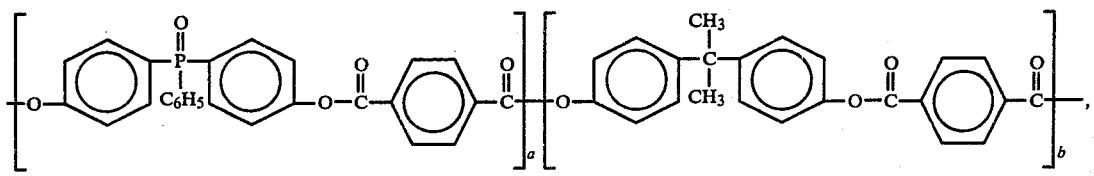

with a ratio of a to b of 70:30, has a melting temperature of 250° C. and a phosphorus content of 5.2 weight percent. Since its structure is still crystalline, the last-mentioned polyarylene ester cannot be characterized by a glass transition temperature but only by a melting temperature. The higher phosphorus content of the polyarylene esters of the invention results in better flame resistance, and their higher glass transition temperature results in improved processing properties.

The polyarylene esters in accordance with the invention exhibit considerably less tendency to crystallize than those which contain only one type each of groups A and B. This is due to an imperfection in the crystalline structure, which in turn is due to a reduced periodicity of the chain structure.

The new polyarylene esters can be processed in the thermoplastic state below their decomposition temperature, at temperatures ranging from about 200° to 380° C., into sheets, fibers, sections or other shapes which are distinguished by good self-extinguishing properties.

The bisphenol HO—A—OH which enters into the composition of the polyarylene esters of the invention is formed at least in part of compounds of the structure

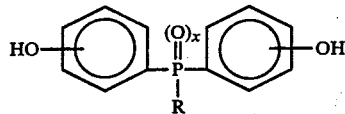

wherein R may be a methyl, chloromethyl, benzyl, or phenyl group, for example. Methyl and phenyl are preferred. The aromatic groups of the compound may optionally carry further substituents, such as annellated (i.e. condensed) aromatic ring systems, methyl groups, or halogen atoms, and particularly bromine or chlorine. The phenolic hydroxyl groups are preferably in a position para to the phosphorus atoms. The oxidized form of the compound, where x is 1, is preferred.

Part of the phosphorus-containing groups A may be replaced by the phosphorus-free groups cited for B. While this will reduce the phosphorus content of the polyarylene ester, it will also further reduce its tendency to crystallize.

As a bisphenol free of phosphorus, a compound of the type

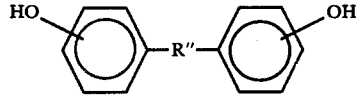

can be introduced, in which R" is a difunctional hydrocarbon group which contains from 5 to 15 carbon atoms and a number of hydrogen atoms which is at most equal in number to the number of carbon atoms. An example of such a material is phenolphthalein.

An upper limit is imposed on the amount of the phosphorus-free groups A in that the phosphorus content must not be less than 1 weight percent. It is preferably over 2 weight percent, usually over 4 weight percent, and more particularly between 5 and 7 weight percent. The amount of the phosphorus-containing groups A is preferably over 50 mole percent, and more particularly over 70 mole percent, of the total of groups A.

The dicarboxylic acids HOOC—B—COOH on which the polyarylene esters are formally based and which largely account for their advantageous properties are either polynuclear aromatic dicarboxylic acids linked by bridging groups R' or, if they do not have this structure, are always mixtures of two or more of the other carboxylic acids of the formula given. The melting temperature lowering effect is usually fully obtained with just two different acids of the type last-mentioned. The effect is promoted by distinct structural differences between the groups B involved. For example, a mixture of terephthalic acid and isophthalic acid is very effective. The amount of each type of groups B involved is preferably not under 10 mole percent, based on the total of groups B. Amounts ranging from 25 to 75 weight percent, and particularly a ratio of 50:50, are preferred.

The polyarylene esters are prepared in principle by polycondensation of bisphenols HO—A—OH with aromatic dicarboxylic acids HOOC—B—COOH, or of functional derivatives of said bisphenols or dicarboxylic acids capable of condensing to form ester groups. Particularly advantageous is the Schotten-Baumann reaction between bisphenols HO—A—OH and dicarboxylic acid dichlorides ClCO—B—COCl in the presence of an at least equivalent amount of a base in an appropriate solvent. Suitable solvents are, for example, aliphatic chlorinated hydrocarbons such as methylene chloride, chloroform, tetrachloroethylene, and tetrachloroethane, or aromatic hydrocarbons such as toluene. Suitable bases are sodium or potassium hydroxide, pyridine and triethylamine. The reaction temperature may range from 0° to 150° C. and preferably ranges from 20° to 100° C.

To obtain a high molecular weight, and hence good plastics properties, the purity of the starting compounds should be as high as possible. In particular, there should be no monofunctional impurities which enter into the reaction but act as chain stoppers. For the same reason, the molar ratio between the bisphenols and the total dicarboxylic acid derivatives should be close to 1:1, as is generally known from the chemistry of polycondensation reactions. The molecular weight of the polyarylene esters should not be under 10,000 and preferably ranges from 20,000 to 80,000. To obtain such molecular weights, condensation times between 0.1 and 10 hours will be required. Often the plastics properties, and especially the strength properties, of the products can be further improved by postcondensation for from 10 to 90 minutes at from 250° to 350° C., optionally under vacuum. The linear macromolecules formed usually contain hydroxyl or carboxyl groups as terminal groups, which, if desired, may subsequently be etherified or esterified. Minor amounts of monofunctional phenols or carboxylic acid may also be selectively added for the formation of terminal groups.

The polymer molecules formed usually remain dissolved during the condensation while the hydrochloride of the base precipitates and can be filtered off. The polymer can be recovered by precipitation with a non-solvent, for example, or by evaporation of the solvent.

Further possibilities for the synthesis of the new polyarylene esters are the melt-condensation processes known from the literature, for example, melt condensation by conversion of the corresponding bisphenol diacetate and dicarboxylic acids, or reaction of the bisphenols with dicarboxylic phenyl esters. A drawback of these methods is the protracted heating of the condensation batches to high temperatures, which may reach 350° C. over 10 hours, and the need to eliminate, by distillation from the highly viscous reaction mixtures, the low molecular weight compounds split off during the condensation.

A better understanding of the present invention and of its many advantages will be had by referring to the following specific Examples, given by way of illustration.

EXAMPLE 1

0.015 mole of dihydroxytriphenylphosphine oxide, 0.035 mole of bisphenol O (dihydroxydiphenyl ether), and 2.4 moles of pyridine were dissolved in 500 ml of tetrachloroethylene and reacted at 100° C. with 0.25 mole of terephthalic acid dichloride and 0.025 mole of isophthalic acid dichloride (dissolved in 500 ml tetrachloroethylene). After 1 hour, 2 mole percent of the above bisphenol mixture (based on the amount initially used) was added and, after 15 minutes, 5 mole percent of benzoyl chloride (based on the initial amount of the acid chloride) was added. The reaction mixture was introduced into 10 liters of methanol and the precipitated polyester was separated, washed free of chloride with water, and dried.

EXAMPLE 2

Example 1 was repeated, except that 0.035 mole of bisphenol A (2,2-di-[4-hydroxyphenyl]propane) was used in place of bisphenol O.

EXAMPLE 3

A solution of 0.025 mole of terephthalic acid dichloride and 0.025 mole of isophthalic acid dichloride was added dropwise within 1 hour at room temperature to 0.05 mole of dihydroxytriphenylphosphine oxide dissolved in 0.32 mole of pyridine and 100 ml of methylene chloride. The mixture was then stirred for 2 hours at room temperature. To convert any acid chloride terminal groups which might still have been present, a further 2 mole percent of dihydroxytriphenylphosphine oxide (based on the amount initially used) was then added. For the purpose of acetylation of the phenolic hydroxylene groups, 5 mole percent of acetyl chloride (based on the initial amount of the acid chlorides) was added after 10 minutes. The polyester formed was precipitated in a methanol/water mixture, washed with water containing hydrochloric acid, and then with distilled water, and dried.

EXAMPLE 4

Example 3 was repeated, except that 0.025 mole of oxybis-(para-phenylenecarbonyl chloride) was used in place of the mixture of isophthalic acid dichloride and terephthalic acid dichloride. The polyester was precipitated, first from gasoline and then from a methanol/water mixture.

| Example | Phosphorus content, wt. % | Glass transition* temperature, °C. | Decomposition** temperature, °C. | Char Residue Value*** % | Crystallinity |
|---|---|---|---|---|---|
| 1 | 2.6 | 165 | 410 | 38 | Mild |
| 2 | 2.4 | 160 | 420 | 32 | Partly crystalline |
| 3 | 7.2 | 175 | 400 | 36 | Amorphous |
| 4 | 5.8 | 125 | 390 | 37 | Amorphous |

*As determined by differential scanning calorimetry
**As determined by differential scanning calorimetry and thermogravimetric analysis
***Pyrolysis residue after 30 min. at 800° C. under $N_2$.

EXAMPLE 5

An amorphous polymer was obtained using the procedure of Example 3 by employing 0.025 mol of naphthalene-1,5-dicarboxylic acid dichloride instead of 0.025 mol of isophthalic acid dichloride.

EXAMPLE 6

Similarly following the procedure of Example 3, an amorphous polymer was obtained by replacing the isophthalic acid dichloride with 0.025 mol of diphenyl-4,4'-dicarboxylic acid dichloride.

EXAMPLES 7-9

In each case, amorphous polymers were obtained employing the procedure of Example 4 but by replacing the 0.05 mol of oxybis-(para-phenylenecarbonyl chloride) by 0.05 mol of, respectively, sulfonyl-bis-p-benzoyl chloride, 2,2-isopropylidene-bis-p-benzoyl chloride, and benzophenone-4,4'-dicarboxylic acid dichloride.

EXAMPLE 10

An amorphous to weakly crystalline polymer was obtained following the procedure of Example 1 but replacing the 0.035 mol of bisphenol O by 0.035 mol of phenolphthalein.

What is claimed is:

1. A polyarylene ester polymer of the formula

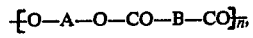

said polymer having a phosphorus content greater than 1 percent by weight and having terminal groups which are hydroxyl or carboxyl groups, or are groups obtainable by reaction of said polymer with a monofunctional phenol or carboxylic acid, wherein
   n has a mean value over 20;
   A represents at least in part a group of the structure

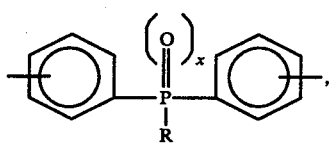

wherein R represents lower alkyl, chlorinated lower alkyl, aryl, aryl substituted by methyl or halogen, or aralkyl, and x is 0 or 1, and the rest, if any, of A comprises at least one member selected from the group of groups of the structure given below for B or the structure

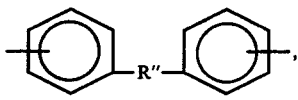

wherein R″ is a difunctional hydrocarbon group which contains from 5 to 15 carbon atoms and a number of hydrogen atoms which is at most equal in number to the number of carbon atoms; and group B represents bivalent aromatic groups having at least two different structures of the formulas

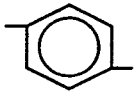

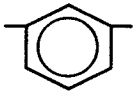

or is at least one group with the structure

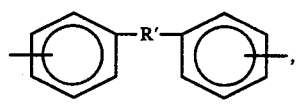

wherein R′ is an oxygen atom, a sulfur atom, or a sulfonyl, carbonyl, or isopropylidene bridging group.

2. A method for making a phosphorus-containing polyarylene ester as in claim 1 which comprises polycondensing a bisphenol HO—A—OH with an aromatic dicarboxylic acid HOOC—B—COOH, wherein A and B have the meanings given in claim 1, or polycondensing a functional derivative of said bisphenol or dicarboxylic acid capable of condensing to form ester groups.

3. A method as in claim 2, wherein corresponding carboxylic acid chlorides ClCO—B—COCl are polycondensed in the presence of an amount of a base at least equimolar to the carboxylic acid chloride groups.

4. A polymer as in claim 1 wherein R is phenyl.
5. A polymer as in claim 1 wherein x is 1.
6. A polymer as in claim 1 wherein R′ is

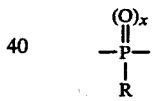

7. A polymer as in claim 6 wherein R is phenyl.
8. A polymer as in claim 6 wherein x is 1.

* * * * *